United States Patent
Omura et al.

(10) Patent No.: US 7,541,336 B2
(45) Date of Patent: Jun. 2, 2009

(54) SUBSTANCE FKI-1033 AND PROCESS FOR PRODUCING THE SAME

(75) Inventors: Satoshi Omura, Tokyo (JP); Kazuro Shiomi, Tokyo (JP); Rokuro Masuma, Tokyo (JP)

(73) Assignee: The Kitasato Institute, Tokyo (JP)

( * ) Notice: Subject to any disclaimer, the term of this patent is extended or adjusted under 35 U.S.C. 154(b) by 117 days.

(21) Appl. No.: 10/532,662

(22) PCT Filed: Nov. 12, 2002

(86) PCT No.: PCT/JP02/11777

§ 371 (c)(1), (2), (4) Date: Jan. 19, 2006

(87) PCT Pub. No.: WO2004/044214

PCT Pub. Date: May 27, 2004

(65) Prior Publication Data

US 2006/0111280 A1    May 25, 2006

(51) Int. Cl.
*A61K 38/00*    (2006.01)
*A61K 51/00*    (2006.01)

(52) U.S. Cl. .................... 514/9; 514/2; 424/1.69
(58) Field of Classification Search .......... 514/9
See application file for complete search history.

(56) References Cited

U.S. PATENT DOCUMENTS 5,116,815 A    5/1992    Takagi et al.

FOREIGN PATENT DOCUMENTS

| DE | WO 01/62268 A1 * | 8/2001 |
| DE | WO 02/00202 A1 * | 1/2002 |
| EP | 382173 | 8/1990 |
| WO | WO 200162268 A1 * | 8/2001 |
| WO | WO 200200202 A1 * | 1/2002 |

OTHER PUBLICATIONS

Kanaoka M. et al., Bassianolide, a New Insecticidal Cyclodepsipeptide from *Beauveria Bassiana* and *Verticillium lecanii*. Agric. Biol.Chem. 1978, vol. 42, No. 3, pp. 629 to 635.

Schmitt M. et al., Binding Sites for Ca2+-Channel Effectors and Ryanodine in Periplaneta Americana—Possible Targets for New Insecticides. Pestic. Sci. 1996, vol. 48, No. 4, pp. 375 to 388.

Higashida H. et al., Molecular Basis of Ion Channels and Receptors Involved in Nerve Excitation, Synaptic Transmission and Muscle Contraction, Annals of the New York Academy of Sciences, vol. 707.

Takeshima H., Proteins, Nucleic Acids and Enzymes, 43: 1603-1609, 1998.

* cited by examiner

*Primary Examiner*—Cecilia Tsang
*Assistant Examiner*—Maury Audet
(74) *Attorney, Agent, or Firm*—Young & Thompson

(57) ABSTRACT

The present invention is comprised of culturing microorganism having ability to produce FKI-1033 substance represented by the formula:

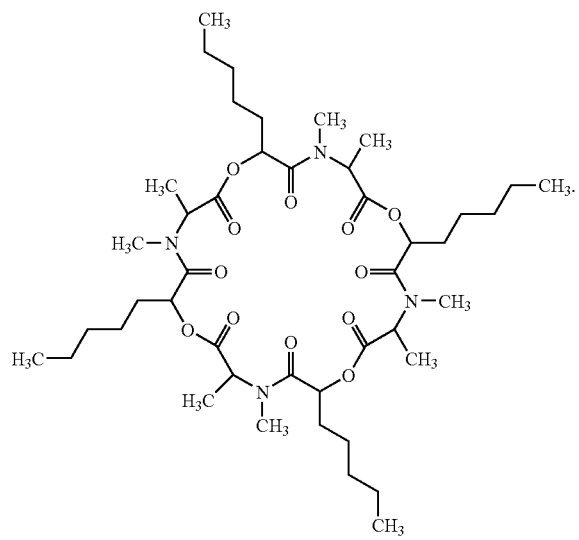

in a medium, accumulating FKI-1033 substance in the cultured medium, and isolating FKI-1033 substance from the cultured mass. The thus obtained FKI-1033 substance has ryanodine binding inhibition activity, insecticidal activity and anthelmintic activity, and is expected as useful drugs as agrochemicals, veterinary drugs and medicaments in effectiveness and toxicity.

3 Claims, No Drawings

SUBSTANCE FKI-1033 AND PROCESS FOR PRODUCING THE SAME

TECHNICAL FIELD

The present invention relates to novel FKI-1033 substance, which is effective for use in agrochemicals, veterinary medicines and pharmaceuticals having an activity of ryanodine binding inhibition, an insecticidal activity and anthelmintic activity, and production thereof.

BACKGROUND ART

Insecticides have contributed undoubtedly to increase production of food resources and stable supply. However, insecticides have brought about large problems such as residual toxicity and destruction of ecological systems.

Parasitosis has been reduced as a result of improvement in environmental hygiene and progress of anthelmintics, but recently afferent parasitosis, zoonotic parasitosis, optimistic parasitosis and parasitosis derived from perishables are increasing, and as a result various parasitoses have become an issue. In livestock farming and agriculture, parasitosis causes great economic burden at present. Among parasitoses, with regard to helminth infection, many compounds such as ivermectin, mebendazole, praziquantel, etc. are used.

However, presently used anthelmintic agents are not always satisfactory in view of effectiveness and toxicities, and new agents are still demanded.

DISCLOSURE OF THE INVENTION

A ryanodine receptor is an ion channel which releases $Ca^{2+}$ from the intracellular store to the cytoplasm with increased $Ca^{2+}$ level in the cytoplasm, and was discovered as a receptor of plant alkaloid, ryanodine, that exhibits the insecticidal activity. In mammals, three types of the ryanodine receptor, i.e. type 1 (the skeletal muscular type), type 2 (the myocardial type) and type 3 (the cerebral type), which were coded independently in the gene, are known as a result of gene cloning. Primary structure of the ryanodine receptor has been elucidated (Takeshima, H. Ann. N.Y. Acad. Sci. 707, 165-177, 1993). It is identified in insects and helminths as the ryanodine receptor which does not belong to the above three types (Takeshima, H. Proteins, Nucleic Acids and Enzymes, 43: 1603-1609, 1998).

Consequently, it was reported that among substances inhibiting the binding of ryanodine to the ryanodine receptor, those having high selectivity to insects and helminths were expected as insecticides and anthelmintic substances (M. Schmitt et al. Pesticide Sci. 48: 375-385, 1996).

We have focused to study the ryanodine receptor and continued to explore the ryanodine binding inhibitors from microbial culture products in order to obtain novel drugs, which were satisfied in the effectiveness and toxicity of the drug, and as a result, we have found that a novel compound, FKI-1033 substance, which was produced by the strain of fungus FKI-1033, had an activity of ryanodine binding inhibition as well as having insecticidal activity and anthelmintic activity, and completed the present invention.

An aspect of the present invention is providing novel FKI-1033 substance, which is effective for use in agrochemicals, veterinary medicines and pharmaceuticals having an activity of ryanodine binding inhibition, an insecticidal activity and anthelmintic activity, and production thereof.

FKI-1033 substance can be obtained by culturing a microorganism belonging to a genus of fungi having ability to produce FKI-1033 substance in a medium, accumulating FKI-1033 substance in the cultured mass and isolating FKI-1033 substance from the cultured mass.

An object of the present invention is to provide novel FKI-1033 substance represented by the following chemical structure:

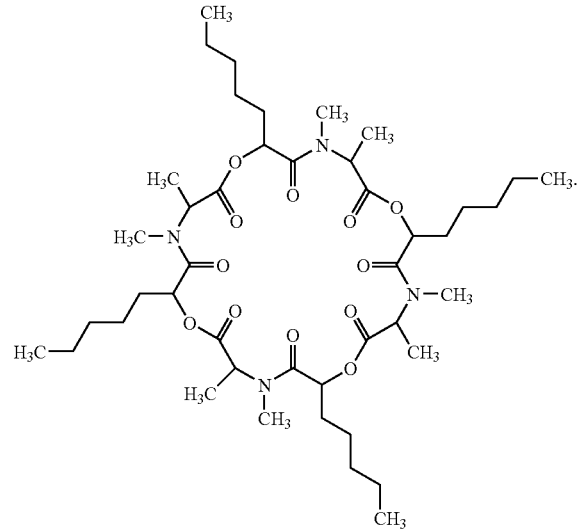

Another object of the present invention is to provide a process for production of novel FKI-1033 substance comprising culturing a microorganism having ability to produce FKI-1033 substance in a medium, accumulating FKI-1033 substance in the cultured medium and isolating FKI-1033 substance from said cultured mass.

Further object of the present invention is to provide a microorganism *Verticillium* sp. FKI-1033 FERM BP-8291 belonging to the *Verticillium* genus of fungi.

Further object of the present invention is to provide the microorganism *Verticillium* sp. FKI-1033 having ability to produce FKI-1033 substance and belonging to the *Verticillium* genus of fungi.

Further object of the present invention is to provide the microorganism *Verticillium* sp. FKI-1033 FERM BP-8291 having ability to produce FKI-1033 substance and belonging to the *Verticillium* genus of fungi.

Further object of the present invention is to provide the process for production of novel FKI-1033 substance wherein the microorganism having ability to produce FKI-1033 substance is *Verticillium* sp. FKI-1033 FERM BP-8291 or its mutant strain having ability to produce FKI-1033 substance.

Further object of the present invention is to provide FKI-1033 substance having an activity of ryanodine binding inhibition and FKI-1033 substance having insecticidal activity and anthelmintic activity.

Further object of the present invention is to provide use of FKI-1033 substance for production of agrochemicals, veterinary medicines and pharmaceuticals having insecticidal activity and anthelmintic activity among substances inhibiting ryanodine binding to the ryanodine receptor.

Further object of the present invention is to provide FKI-1033 substance for production of agrochemicals, veterinary medicines and pharmaceuticals having insecticidal activity and anthelmintic activity among substances inhibiting ryanodine binding to the ryanodine receptor.

The microorganism having ability to produce novel FKI-1033 substance represented by the formula hereinabove (hereinafter designates as "FKI-1033 substance producing microorganism") is fungus, and can be the microorganism having ability to produce FKI-1033 substance of the present invention without specific limitation. Preferable example of the strain used for production of FKI-1033 substance of the present invention is the strain *Verticillium* sp. FKI-1033, which was newly isolated from a soil sample collected at Kagoshima Pref. by the inventors of the present invention. Taxonomical properties of the strain are as follows.

(1) Morphological Characteristics

The strain showed relatively good growth on potato glucose agar medium, cornmeal agar medium, Miura's agar medium, Malt extract agar medium and oatmeal agar medium. Conidiogenesis on each medium was moderate.

Microscopic observation of colonies grown on the malt extract agar medium was shown hyphae with septa, and conidiophores were born from the aerial mycelia with branch in some times. The phialide was observed directly from aerial hyphae or alone or two to four verticillations in the middle part or the top of conidophores. Length of the phialide was 25-80 μm with slightly swelling in the base (2.0-2.8 μm) and narrowing with the cuneate shape of the top. Conidia were suglobose to oval (2.5-4.0×2.0-3.0 μm) and formed viscous conidial mass from the top of phialide.

(2) Culture Properties on Various Agar Media

Macroscopic observations of the strain cultured on various agar media at 25° C. for 7 days are shown in Table 1.

TABLE 1

| Medium | Growth condition on the medium (diameter of colony) | Color of surface of colony | Color of reverse side of colony | Soluble pigment |
|---|---|---|---|---|
| Potato - glucose agar | Moderate (42–44 mm), Floccose - velvety, Entire smooth penumbra | White | Pale yellowish brown | None |
| Cornmeal agar | Moderate (39–42 mm), Powdery - velvety, Entire smooth penumbra | White | Pale yellowish brown | None |
| Miura's agar | Moderate (44–45 mm), Powdery - velvety, Entire smooth penumbra | White | White | None |
| Malt extract agar | Moderate (42–46 mm), Floccose - velvety, Entire smooth penumbra | White | White - Pale yellowish brown | None |
| Oatmeal agar | Moderate (43–46 mm), Floccose velvety, Entire smooth penumbra | White | White | None |

(3) Physiological Properties (1) Optimum Growth Condition

Optimum growth conditions of the strain were pH 5-7 and 18.5-29.0° C.

(2) Growth Range

The pH range for growth of the strain was 4-10, and the temperature range was 6.5-31° C.

(3) Nature: Aerobic

As a result of comparison with the morphological properties, culture properties and physiological properties of the strain FKI-1033 and known strains, the present strain was identified as a strain belonging to genus *Verticillium*, and was referred to *Verticillium* sp. FKI-1033. The strain was deposited as *Verticillium* sp. FKI-1033 in the International Patent Organism Depositary, National Institute of Advanced Industrial Science and Technology of AIST Tsukuba Central 6, 1-1, Higashi 1-chome, Tsukuba-shi, Ibaraki-ken, 305-8566 Japan. Date of depository was Oct. 21, 2002 as deposition No. FERM BP-8219.

Production of FKI-1033 substance of the present invention can be performed by culturing FKI-1033 substance producing microorganism belonging to fungi in a medium, isolating from the cultured mass thereof and purifying the same. Since general taxonomical properties of microorganisms are very easily mutated and are not stable, not only the natural mutants but also the artificial mutants obtained by conventional ultraviolet irradiation or treatment with mutant inducer such as N-methyl-N'-nitro-N-nitrosoguanidine, including all FKI-1033 substance producing strains belonging to fungi can be used in the present invention.

Nutrient sources suitable for production of FKI-1033 substance can be nutrient sources of fungi. For example, the nutrient sources can be used are commercially available nitrogen sources such as peptone, meat extract, corn steep liquor, cotton seed powder, peanuts powder, soybean meal, yeast extract, NZ-amine, casein hydrolyzate, sodium nitrate, ammonium nitrate and ammonium sulfate, carbohydrates such as glycerin, starch, glucose, galactose and mannose, or carbon sources such as fatty acids, and inorganic salts such as sodium chloride, phosphate, calcium carbonate and magnesium sulfate, alone or in combination thereof.

If necessary, trace metal salts, animal, vegetable and mineral oil as an antifoaming agent can be added. These are preferable substances which can be used by the producing microorganism and useful for production of FKI-1033 substance, and all known materials for culturing fungi can be used. In a mass production of FKI-1033 substance, liquid culture is preferably applied. Culturing temperature can be applied within a range of the growth of the producing strain and the production of FKI-1033 substance. Culturing condition hereinabove described can be optionally selected depending on properties of FKI-1033 substance producing microorganism.

FKI-1033 substance can be extracted by using water immiscible organic solvent such as chloroform and ethyl acetate from the cultured liquid. In addition to the above extraction, known isolation methods used for collection of fat-soluble substance such as adsorption chromatography, partition chromatography, gel filtration chromatography, scraping from thin layer chromatography, centrifugal counter-current chromatography and high performance liquid chromatography can be applied in combination or repeatedly to obtain purified substance.

Physicochemical properties of FKI-1033 substance of the present invention are as follows.

(1) Nature: colorless oil
(2) Molecular weight: 875.5397 (M+Na, high resolution fast atom bombardment mass spectrometry)
(3) Molecular formula: $C_{44}H_{76}N_4O_{12}$
(4) Specific rotation: $[\alpha]_D^{25}=-53.00$ (c=0.2, methanol)
(5) Ultraviolet absorption spectrum (in methanol): maximum absorption at 202 nm (ε=19700)
(6) Infrared absorption spectrum (KBr): maximum absorption at 3467, 2956, 2933, 2862, 1743, 1662, 1464, 1416, 1205, 1084 $cm^{-1}$
(7) $^1H$ proton NMR: Chemical shift in deuterated chloroform and spin coupling constant were measured by using Unity Inova 600 NMR spectrometer, Varian Inc., the U.S. Chemical shift (ppm) and spin coupling constant (Hz) are shown in Table 2.

(8) 13C NMR: Chemical shift in deuterated chloroform was measured by using Unity Inova 600 NMR spectrometer, Varian Inc., the U.S. Chemical shift (ppm) is shown in Table 2.

(9) Solubility in solvent: Soluble in methanol, ethanol, ethyl acetate and chloroform. Hardly soluble in water and n-hexane.

(10) Color reaction: Positive for sulfuric acid.

TABLE 2

| $^{13}$C | $^1$H |
|---|---|
| 171.2 s | |
| 171.0 s | |
| 170.8 s × 4 | |
| 170.0 s | |
| 169.9 s × 2 | |
| 169.8 s | |
| 169.3 s × 3 | |
| 169.2 s | |
| 71.6 d | 5.11 dd (1H, J = 2.5, 10.6) |
| 71.3 d × 3 | 5.42 m (3H) |
| 71.0 d | 5.45 dd (1H, J = 5.3, 8.4) |
| 70.8 d | 5.3G dd (1R, J = 5.3, 9.0) |
| 70.7 d | 5.32 dd (1H, J = 3.3, 10.1) |
| 54.4 d | 4.56 q (1R, J = 7.3) |
| 51.94 d × 3 | 5.40 q (3H, J = 7.2) |
| 51.85 d | 5.54 q (1H, J = 7.4) |
| 51.76 d | 5.30 q (1H, J = 7.4) |
| 51.5 d | 5.53 q (1H, J = 7.3) |
| 31.5 q | 3.18 s (3H) |
| 31.40 t × 5 | 1.31 m (10H) |
| 31.36 t × 2 | 1.3C m (4H) |
| 31.2 t | 1.78 m (2H) |
| 31.1 t | 1.78 m (2H) |
| 31.0 t × 3 | 1.78 m (6H) |
| 30.98 t | 1.78 m (2H) |
| 30.97 q | 2.96 s (3H) |
| 30.92 t | 1.78 m (2H) |
| 30.73 q × 3 | 2.91 s (9H) |
| 30.66 q | 3.01 s (3H) |
| 29.4 q | 2.89 s (3H) |
| 25.1 t | 1.30 m (2H) |
| 24.83 t | 1.30 m (2H) |
| 24.82 t | 1.30 m (2H) |
| 24.76 t × 4 | 1.30 m (8H) |
| 22.42 t × 4 | 1.30 m (8H) |
| 22.39 t × 3 | 1.30 m (6H) |
| 15.9 q | 1.59 d (3H, J = 7.3) |
| 15.0 q | 1.41 d (3H, J = 7.4) |
| 14.8 q | 1.45 d (3H, J = 7.3) |
| 14.2 q × 3 | 1.38 d (9H, J = 7.2) |
| 14.0 q | 1.39 d (3H, J = 7.4) |
| 13.93 q × 3 | 0.88 m (9H) |
| 13.90 q | 0.88 m (3H) |
| 13.88 q × 3 | 0.88 m (9H) |

In the table, each symbol shows: s: singlet, d: doublet, t: triplet, q: quartet, m: multiplet, H: number of proton, J: coupling constant (Hz).

As a result of detailed discussion and examination of various physicochemical properties and spectral data of FKI-1033 substance, chemical structure of FKI-1033 substance was determined to be represented by the following formula. In the proton and $^{13}$C NMR spectra of FKI-1033 substance, 1.75 times signal strength above the molecular formula were shown. This may be due to that FKI-1033 substance may exist in the form of two types of the conformational isomer with a ratio of 3:4. In one conformational isomer, the signal number can only be observed in ¼ thereof. This suggests that the conformation is four-fold rotation symmetry.

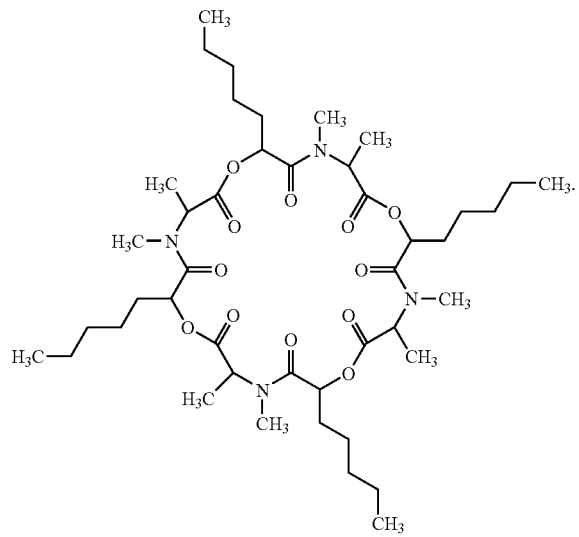

As described hereinabove, various physicochemical properties of FKI-1033 substance are described in detail, and no compound identical with these properties has been reported, consequently FKI-1033 substance was determined as a novel substance.

The ryanodine binding inhibition activity of FKI-1033 substance of the present invention will be explained in detail as follows.

(1) Preparation of the Crude Ryanodine Receptor Fraction of the Insect was Performed as Follows.

The thorax and legs of ten adult insects of *Periplaneta americana* were frozen with liquid nitrogen and finely cut, and homogenized three times in 15 ml of 50 mM Tris HCl buffer (pH 7.4) containing 4 μg/ml leupeptin and 3 μg/ml pepstatin by using a knife homogenizer at 0° C., 24,000 rpm for 30 sec. The homogenate was filtered using double layered cotton cloth and the filtrate was centrifuged at 4° C., 3,000 rpm for 20 minutes. The obtained supernatant was centrifuged at 4° C., 30,000 rpm for 30 minutes and the precipitate suspended in 1 ml of 20 mM Tris HCl buffer (pH 8.0) containing 0.3 M sucrose, 500 μM calcium chloride and 1.5 M potassium chloride and homogenized with glass potter to obtain crude ryanodine receptor fraction. The crude ryanodine receptor fraction was used by diluting about 7 times with the buffer A (20 mM Tris-HCl buffer (pH 8.0) containing 4 μg/ml aprotinin, 4 μgμml leupeptin, 0.3 M sucrose and 500 μM calcium chloride) immediately before use.

(2) Preparation of Mammalian Crude Ryanodine Receptor Fraction was Performed as Follows.

Muscles of the hind legs of ICR mouse were finely cut, and 3.0 g thereof was homogenized at 0° C., 1,000 rpm for 3×30 sec using glass homogenizer in 15 ml of buffer B (20 mM Tris-HCl buffer (pH 8.0) containing 4 μg/ml aprotinin and 4 μg/ml leupeptin). The homogenate was transferred into the micro test tube, and the glass homogenizer was also washed with the 7.5 ml of buffer B, and the washed solution was also added to the micro test tube, which was stirred, then centrifuged by using ultracentrifuge cooled at 4° C., 25,000×g for 40 min. 2.4 ml of the buffer B was added to the obtained precipitate and suspended to obtain the crude ryanodine receptor fraction of mouse origin.

(3) Binding Activity of Crude Ryanodine Receptor of *Periplaneta americana* Was Assayed as Follows.

70 μl of the buffer A, 10 μl of ethanol solution of 0.1 nM ryanodine and 10 μl of 20 nM [9,21-$^3$H] (N) ryanodine were added into the 96 well microplate (Corning Inc. the U.S.). 10 µl of crude ryanodine receptor fraction of *Periplaneta americana* was added to initiate the reaction, and shaken at room temperature for 90 min. by using microplate mixer. The reaction mixture was filtered with glass fiber filter (Wallac Inc, Printed Filtermat B) using harvester 96®Mach III M (Tomtech Inc.), and washed three times with 300 µl of 20 mM Tris HCl buffer (pH 8.0) at low temperature. The filter was dried with using the microwave oven. A scintillator sheet (Wallac Inc. the U.S., MeltiLex™ B/HS) was overlaid thereon and the sheet was fused on the hot plate. Radioactivity was measured by measuring fluorescence intensity of the filter with using scintillation counter (Wallac Inc. the U.S., MicroBeta™ TriLux)

The ryanodine binding inhibition activity of FKI-1033 substance was assayed by adding FKI-1033 substance initially in the assay of ryanodine binding activity and calculated by the following equation as compared with the control ryanodine binding activity.

Activity of ryanodine binding inhibition=(1−(Radioactivity at addition of FKI-1033 substance/Radioactivity of control))×100

According to the calculated result of the above equation, FKI-1033 substance showed the ryanodine binding inhibition activity, $IC_{50}=4.2$ µM, against the ryanodine receptor of *Periplaneta americana* origin.

(4) Binding Activity of Crude Mammalian Ryanodine Receptor was Assayed aAs Follows.

70 µl of the buffer A, 10 µl of ethanol solution of 0.1 nM ryanodine and 10 µl of 20 nM $[9,21-^3H]$ (N) ryanodine were added into the 96 well microplate (Corning Inc. the U.S.). 10 µl of crude ryanodine receptor fraction of mouse origin was added to initiate the reaction, and shaken at room temperature for 90 min. by using microplate mixer. The reaction mixture was filtered with glass fiber filter (Wallac Inc, Printed Filtermat B) using Harvester 96®Mach III M (Tomtech Inc.), and washed three times with 300 µl of 20 mM Tris HCl buffer (pH 8.0) at low temperature. The filter was dried with using the microwave oven. A scintillator sheet (Wallac Inc. the U.S., MeltiLex® B/HS) was overlaid thereon and the sheet was fused on the hot plate. Radioactivity was measured by measuring fluorescence intensity of the filter with using scintillation counter (Wallac Inc. the U.S., MicroBeta™ TriLux).

The ryanodine binding inhibition activity of FKI-1033 substance was assayed by adding FKI-1033 substance initially in the assay of ryanodine binding activity and calculated by the following equation as compared with the control ryanodine binding activity.

Activity of ryanodine binding inhibition=(1−(Radioactivity at addition of FKI-1033 substance/Radioactivity of control))×100

According to the calculated result of the above equation, FKI-1033 substance showed the ryanodine binding inhibition activity, $IC_{50}=53.9$ µM, against the ryanodine receptor of mouse origin.

Consequently, according to the above assay results, FKI-1033 substance was confirmed to exhibit more than ten times potent ryanodine binding inhibition activity against the insect ryanodine receptor than the mammalian ryanodine receptor.

(5) Antimicrobial Activity of FKI-1033 is Shown as Follows.

The paper discs (Advantech Inc., Japan, diameter 6 mm) were soaked with 10 µl of methanol solution (1 mg/ml) of FKI-1033 substance, and the solvent was removed with drying for constant time. Then the discs were put on the agar plate containing each test microorganism. Agar plates were incubated at 35° C. for time. 24 hours, and the diameter of growth inhibition zone surrounding the paper disc was measured. Results are shown in Table 3.

TABLE 3

| Test microorganism | Inhibition zone diameter (mm) |
|---|---|
| *Staphylococcus aureus* ATCC 6538p | — |
| *Bacillus subtilis* ATCC 6633 | — |
| *Micrococcus luteus* ATCC 9341 | — |
| *Mycobacterium smegmatis* ATCC 607 | — |
| *Escherichia coli* NIHJ | — |
| *Escherichia coil* NIHJ JC-2 (IFO 12734) | — |
| *Pseudomonas aeruginosa* IFO 3080 | — |
| *Xanthomonas campestris* pv. oryzae KB 88 | — |
| *Bacteroides fragilis* ATCC 23745 | — |
| *Acholeplasma laidrawii* KB 174 | — |
| *Candida albicans* KF1 | — |
| *Saccharomyces cerevisiae* KF 26 | — |
| *Pyricularia oryzae* KF 180 | — |
| *Aspergillus niger* ATCC 6275 | — |
| *Mucor racemosus* IFO 4581 | — |

As shown in Table 3 hereinabove, FKI-1033 substance exhibited no growth inhibitory activities against various microorganisms.

(6) Anti-nematode and Anti-arthropod Activities of FKI-1033 Substance will be Explained in Detail as Follows.

Methanol solution of FKI-1033 substance was added into 96 well plate (Corning Inc., the U.S.), removed off methanol in vacuo, added 250 µl of test medium (lecithin 0.01%, sodium hydrogen carbonate 7.5 mM, potassium chloride 7.5 mM, calcium chloride dihydrate 7.5 mM and magnesium sulfate heptahydrate 7.5 mM) and shaken for 15 min. 50 µl of buffer containing several nauplii of *Artemia salina*, which were hatched off in the buffer, was added thereto, and about ten nematodes, *Caenorhabditis elegans*, which were bred on agar medium for growth of nematode, were added thereto. Appearance of these organisms were observed after 2 days under microscope, and FKI-1033 substance inhibited growth of the arthropods and nematodes at 20 µg/ml.

Consequently, FKI-1033 substance can be used as pharmaceuticals such as ryanodine binding inhibitor, insecticide or anthelmintic agent.

BEST MODE FOR CARRYING OUT THE INVENTION

The present invention is explained with an example but is not construed as limiting within the example.

Each loopful strain of *Verticillium* sp. FKI-1033 FERM BP-8219 cultured on the agar slant medium was inoculated into a 500 ml Erlenmeyer flask containing 100 ml of liquid medium (pH 6.0) consisting of glucose 2.0%, Polypepton (Nihon Seiyaku Co., Japan) 0.5%, yeast extract (Oriental Yeast Co., Japan) 0.2%, agar 0.1%, potassium dihydrogen phosphate 0.1%, magnesium sulfate heptahydrate 0.05% and water, and shake cultured at 27° C. for 3 days. Each 20 ml of this seed culture liquid was added into each one of 4 flasks of 500 ml Erlenmeyer flask containing each 80 ml of sterilized and deionized water and diluted. Each 10 ml of the diluted seed culture was inoculated into 24 Roux flasks (capacity 1 lit.) containing 240 g of production medium (Italian rice 150 g, tap water 90 ml, iron (II) sulfate heptahydrate 0.9 mg, copper (II) sulfate pentahydrate 0.9 mg and cobalt chloride hexahydrate 0.9 mg), and cultured statically at 27° C. for 13 days.

A mixed solution of methanol:water=2:1 (200 ml) was added to each of the 24 Roux flasks (1 lit.), vigorously agitated and allowed to stand for 3 hours. Methanol was removed in vacuo, and the obtained aqueous solution was extracted twice with equal amount of ethyl acetate. Using anhydrous sodium sulfate, the ethyl acetate solution was dehydrated and dried in vacuo to obtain 2.53 g of dark brown oily substance. This was charged on a silica gel column (φ2.8×14.0 cm) packed with hexane, washed with a mixture of hexane-ethyl acetate (100:75), eluted with a mixture of hexane-ethyl acetate (100:150) and concentrated in vacuo to obtain 183 mg of dark brown oily substance. The substance was charged on Sephadex LH-20 column (φ2.7×92 cm) and eluted with methanol to obtain 86.5 mg of FKI-1033 substance as colorless oily substance.

INDUSTRIAL APPLICABILITY

As explained hereinabove, FKI-1083 substance is produced by culturing the microorganism having ability to produce FKI-1033 substance in the medium, accumulating FKI-1033 substance in the medium, and isolating FKI-1033 substance from the cultured mass. FKI-1033 substance has ryanodine binding inhibition activity, insecticidal activity and anthelmintic activity, and is expected as useful novel FKI-1033 substance for agricultural chemicals, veterinary drugs and medicaments which can be satisfactorily on the point of effectiveness, toxicity, etc.

The invention claimed is:

1. An isolated FKI-1033 substance represented by the formula:

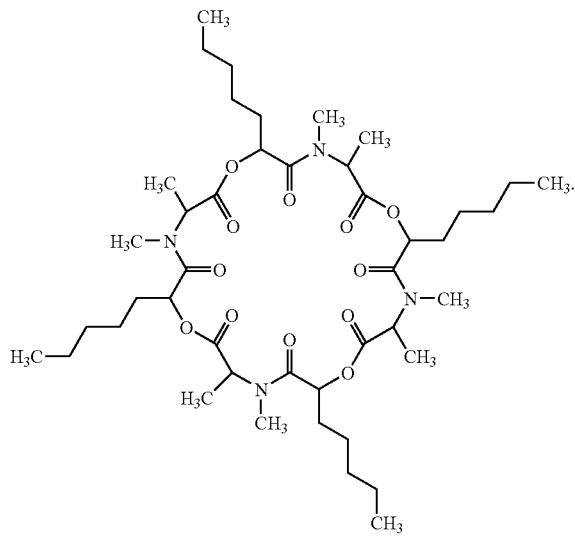

2. A process for production of an isolated FKI-1033 substance represented by the formula:

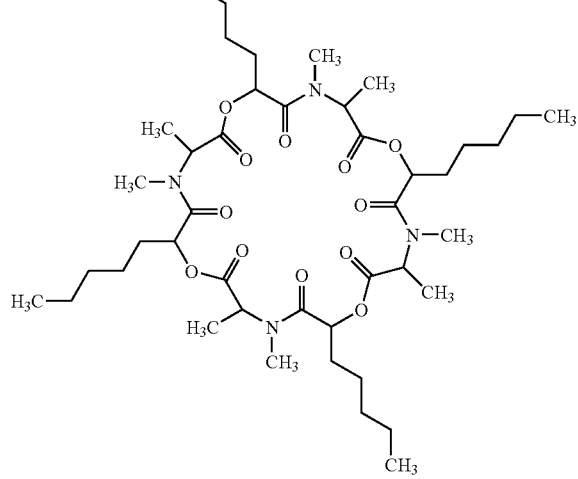

comprising:
culturing a microorganism belonging to fungi and having ability to produce FKI-1033 substance in a medium;
accumulating FKI-1033 substance in the cultured medium; and
isolating FKI-1033 substance from the cultured mass.

3. The isolated FKI-1033 substance according to claim 1, wherein said microorganism capable of producing said FKI1033 substance is *Verticillium* sp. FKI1033 FERM BP8219.

* * * * *